US010965093B2

United States Patent
Brown et al.

(10) Patent No.: US 10,965,093 B2
(45) Date of Patent: Mar. 30, 2021

(54) LIGHT MODULATION FOR IMPROVED PHOTOACOUSTIC FEEDBACK ON LIGHT-INDUCED TREATMENTS AND PROCEDURES

(71) Applicant: INSTITUT NATIONAL D'OPTIQUE, Québec (CA)

(72) Inventors: Robert B. Brown, Quebec (CA); Suzie Dufour, Québec (CA); Pascal Gallant, Québec (CA); Ozzy Mermut, Québec (CA); Pascal Deladurantaye, Québec (CA)

(73) Assignee: INSTITUT NATIONAL D'OPTIQUE, Quebec (CA)

( * ) Notice: Subject to any disclaimer, the term of this patent is extended or adjusted under 35 U.S.C. 154(b) by 103 days.

(21) Appl. No.: 15/973,005

(22) Filed: May 7, 2018

(65) Prior Publication Data

US 2018/0323571 A1 Nov. 8, 2018

Related U.S. Application Data

(60) Provisional application No. 62/502,079, filed on May 5, 2017.

(51) Int. Cl.
*H01S 3/00* (2006.01)
*H01S 3/13* (2006.01)
(Continued)

(52) U.S. Cl.
CPC .......... *H01S 3/1305* (2013.01); *A61B 5/0095* (2013.01); *A61B 18/20* (2013.01);
(Continued)

(58) Field of Classification Search
USPC ................................................ 606/1–12, 17
See application file for complete search history.

(56) References Cited

U.S. PATENT DOCUMENTS 7,357,570 B2   4/2008   Schuele
7,465,299 B2   12/2008  Rovati et al.
(Continued)

FOREIGN PATENT DOCUMENTS

DE           10135944 A1    2/2003

OTHER PUBLICATIONS

Schuele, G. et al., "Optoacoustic real-time dosimetry for selective retina treatment", Journal of Biomedical Optics, Nov./Dec. 2005, vol. 10, No. 6, pp. 064022-1 to 064022-11.
Feng, X. et al., "Self temperature regulation of photothermal therapy by laser-shared photoacoustic feedback", Optics Letters, Oct. 1, 2015. vol. 40, No. 19, pp. 4492-4495.
(Continued)

*Primary Examiner* — Gary Jackson
*Assistant Examiner* — Anant A Gupta
(74) *Attorney, Agent, or Firm* — Brooks Kushman P.C.

(57) ABSTRACT

Methods and systems enabling the real-time monitoring of a light-induced procedure in a biological medium, and/or the acquisition of information related to this biological medium are provided. In some implementations, the light beam used for the procedure is modulated at a modulation frequency selected in view of the photoacoustic frequency response associated with the procedure. The photoacoustic feedback signal from the medium during the procedure is then monitored. This monitoring may involve filtering the photoacoustic feedback signal around the selected feedback modulation frequency. Ratiometric comparisons of the contribution of different frequencies to the photoacoustic feedback signal are also considered.

31 Claims, 10 Drawing Sheets

(51) Int. Cl.
  *H01S 3/137* (2006.01)
  *H01S 3/10* (2006.01)
  *A61F 9/008* (2006.01)
  *A61B 5/00* (2006.01)
  *A61B 18/20* (2006.01)
  *H01S 3/11* (2006.01)
  *H01S 3/067* (2006.01)
  *A61B 18/00* (2006.01)
  *A61B 18/26* (2006.01)

(52) U.S. Cl.
  CPC .......... *A61F 9/008* (2013.01); *H01S 3/10069* (2013.01); *H01S 3/137* (2013.01); *A61B 5/0066* (2013.01); *A61B 5/4836* (2013.01); *A61B 18/26* (2013.01); *A61B 2018/0088* (2013.01); *A61B 2018/00642* (2013.01); *A61B 2018/266* (2013.01); *A61F 2009/00844* (2013.01); *A61F 2009/00863* (2013.01); *H01S 3/067* (2013.01); *H01S 3/11* (2013.01)

(56) References Cited

U.S. PATENT DOCUMENTS

| | | | |
|---|---|---|---|
| 7,771,417 B2 | 8/2010 | Telfair et al. | |
| 7,836,894 B2 | 11/2010 | Brinkmann et al. | |
| 2003/0196477 A1* | 10/2003 | Auner | G01N 29/2418 73/24.06 |
| 2005/0119643 A1* | 6/2005 | Sobol | A61B 18/20 606/9 |
| 2013/0102865 A1* | 4/2013 | Mandelis | G01N 21/1702 600/328 |
| 2014/0058244 A1* | 2/2014 | Krocak | A61B 5/0095 600/407 |
| 2014/0243805 A1 | 8/2014 | Dick et al. | |
| 2015/0342678 A1 | 12/2015 | Deladurantaye et al. | |
| 2017/0042428 A1* | 2/2017 | Kellnberger | A61B 5/7228 |
| 2018/0206816 A1* | 7/2018 | Prus | A61B 8/481 |

OTHER PUBLICATIONS

Brinkmann, R. et al., "Real-time temperature determination during retinal photocoagulation on patients", Journal of Biomedical Optics, Jun. 2012. vol. 17, No. 6, pp. 061219-1 to 061219-10.

Brinkmann, R. et al., "Selective Retina Therapy (SRT): A review on methods, techniques, preclinical and first clinical results", Bull. Soc. Beige Ophtalmol, 2006, vol. 302, pp. 51-69.

Roider,J. et al., "Selective Retina Therapy (SRT) for clinically significant diabetic macular edema", Graefe's Archive for Clinical and Experimental Ophthalmology, 2010, vol. 248, No. 9, pp. 1263-1272.

Veritti, D. et al., "Online optical coherence tomography during subthreshold laser irradiation", European Journal of Ophthalmology, 2011, vol. 22, No. 4, pp. 575-579.

Steiner, P., et al., "Time-resolved ultra-high resolution optical coherence tomography for real-time monitoring of selective retina therapy", Investigative Ophthalmology & Visual Science, 2015, vol. 56, No. 11, pp. 6654-6662.

Serebryakov, V. et al., "Real-time optoacoustic monitoring of the temperature of the retina during laser therapy", Journal of Optical Technology, 2014, vol. 81, No. 6, pp. 312-321.

Xu, M. et al., "Photoacoustic imaging in biomedicine", Review of Scientific Instruments, 2006, vol. 77, No. 4, p. 041101.

Schuele, G., et al., "Optoacoustic control system for selective treatment of the retinal pigment epithelium", BiOS Proc. SPIE 4256, Biomedical Optoacoustics II, 2001.

Besson, J.-P. et al., "Multi-gas sensing based on photoacoustic spectroscopy using tunable laser diodes", Spectrochimica Acta Part A: Molecular and Biomolecular Spectroscopy, 2004, vol. 60, No. 14, pp. 3449-3456.

Langer, G., et al., "Frequency domain photoacoustic and fluorescence microscopy", Biomedical Optics Express, 2016, vol. 7, No. 7, pp. 2692-2702.

Chgarev, N. et al., "Nonlinear frequency-mixing photoacoustic imaging of a crack", Journal of Applied Physics, 2009, vol. 106, No. 3.

* cited by examiner

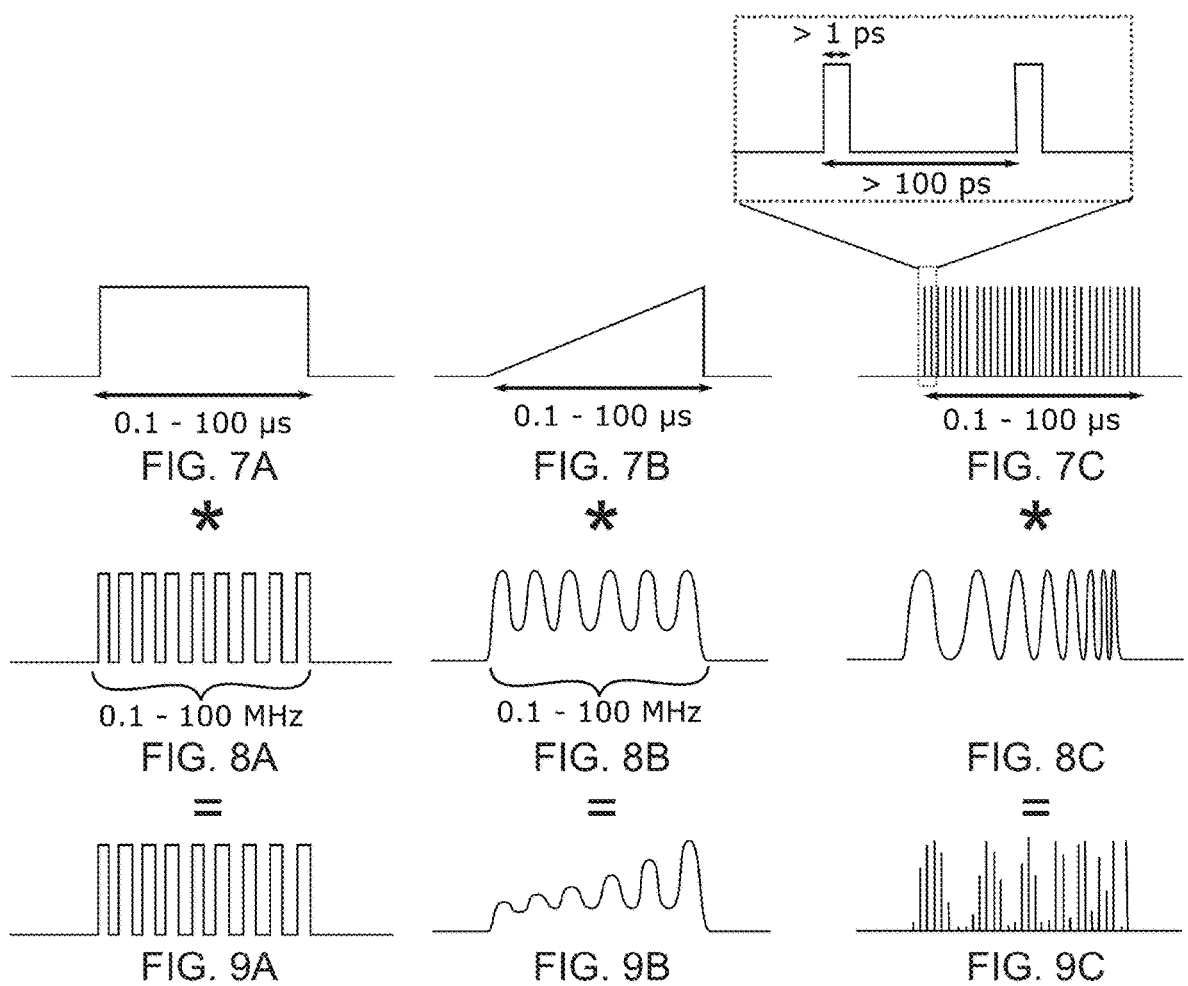

LIGHT MODULATION FOR IMPROVED PHOTOACOUSTIC FEEDBACK ON LIGHT-INDUCED TREATMENTS AND PROCEDURES

CROSS-REFERENCE TO RELATED APPLICATIONS

This application is claims the benefit of U.S. provisional application Ser. No. 62/502,079 filed May 5, 2017, the disclosure of which is hereby incorporated in its entirety by reference herein.

TECHNICAL FIELD

The technical field generally relates to phototherapy procedures and the like and more particularly concerns the use of a modulated light beam for improving feedback mechanisms for such procedures.

BACKGROUND

Lasers are used to treat numerous medical conditions, for example, by precise ablation, photo-disruption or photo-thermal (e.g. photocoagulation) treatment of targeted tissues. Due to high levels of inhomogeneity in the optical absorption and scattering properties both within and between tissues in the same individual, as well as between different individuals, consistent dosing of the laser energy delivered to a target remains challenging. Feedback of absorbed dosage by tissues is thus desired to provide consistent and repeatable treatment regimes.

In ocular procedures, for example, a feedback mechanism is highly desired for treatments such as selective retinal therapy (SRT) and subthreshold micropulse diode laser therapy (SDM), which provide no visual feedback for the ophthalmologist. As a result, these treatments are not commonly applied, although studies have been performed and have demonstrated better outcomes for these treatments compared to the more destructive photocoagulation treatments which are routinely used [Brinkmann, R., J. Roider, and R. Birngruber, SELECTIVE RETINA THERAPY (SRT): A review ON. Bull. Soc. Belge Ophtalmol, 2006, 302: p. 51-69]. In procedures such as SRT, laser induced micro-cavitation (micro-cavitation bubble formation) is used to produce confined cellular damage. Currently, laser pulse damage precludes the use of short treatment pulses (<a few 100 ns) due to the formation of large micro-cavitation bubbles which cause extensive damage around the treatment area, resulting in permanent vision impairment. Longer pulses allow greater control of bubble size [Deladurantaye, P. and O. Mermut, LASER-DIRECTED MICROCAVITATION, 2015, U.S. Patent application 2015/0342678]. However, due to the variability within tissues it remains difficult to ensure that the laser treatment is within the window of effectiveness without a readout measure. Due to stress and thermal confinement dynamics as well as microsecond bubble lifetimes (expansion and collapse), both the thermoelastic and the cavitation pressure waves generated are in the ultrasonic MHz frequency range [Roider, J., et al., Selective retina therapy (SRT) for clinically significant diabetic macular edema. Graefe's Archive for Clinical and Experimental Ophthalmology, 248(9), 2010: p. 1263-1272].

Optical feedback is an obvious choice for laser-based treatments since it is noninvasive and, by nature, present in laser treatments. As micro-cavitation forms, the reflectivity at the treated zone changes. By detecting the back-reflected light transients, one can monitor micro-cavitation occurrences. This technique is suited for micro-cavitation detection but not for detecting temperature changes. Monitoring of reflected light is not necessarily indicative of the absorbed dosage since scattering losses and transmission through the target of interest are not accounted for.

Real-time Optical Coherence Tomography (OCT) is another alternative for monitoring SRT and other phototherapies. Its effectiveness was demonstrated during photocoagulation and sub-threshold laser irradiation. The later treatment is a sub-threshold version of photocoagulation. Both treatments use much longer exposure times than SRT and therefore cause much slower temperature variations [Veritti, D., V. Sarao, and P. Lanzetta, Online optical coherence tomography during subthreshold laser irradiation. European journal of ophthalmology, 2011, 22(4): p. 575-579]. Steiner and his colleagues reported the use of time-resolved high speed OCT to provide feedback during SRT [Steiner, P., et. al., Time-Resolved Ultra-High Resolution optical Coherence Tomography for Real-Time Monitoring of Selective Retina Therapy. Investigative ophthalmology & visual science, 2015, 56(11): p. 6654-6662]. Clinical results have shown that SRT irradiation induces changes in the time-resolved axial OCT scans below the threshold of visual lesions. It is not clear yet if the technique can be sensitive to sub-cavitation tissue changes. As for regular back-reflection measurement, it is not directly indicative of the absorbed dose. Moreover, the maximal permissible exposure (MPE) limits the OCT signal and therefore, most OCT systems are limited to ~100 kHz, this limits the size of micro-cavitation which can be detected to a few micrometers in diameter as cavitation size and duration are directly related according to Rayleigh's equation.

Photoacoustic (PA) signal, also referred as optoacoustic signal, has the advantage that it is directly dependent on the absorbed energy dosage for short laser pulses and has been successfully used for treatment dosimetry. In SRT, micro-cavitations were detected from PA signal amplitudes or signal repeatability [Schuele, G., et al., Optoacoustic real-time dosimetry for selective retina treatment. Journal of biomedical optics, 2005, 10(6): p. 064022-064022-11], but these methods are either limited to micro-cavitation detection or lack sensitivity, especially near micro-cavitation threshold. It was reported that real time PA dosimetry within a therapeutic window was challenging with long treatment pulses (i.e. exposures of the order of 0.1 µs or greater) [Serebryakov, V., É. Boĭko, and A. Yan, Real-time optoacoustic monitoring of the temperature of the retina during laser therapy. Journal of Optical Technology, 2014, 81(6): p. 312-321], where pulse lengths are significantly longer than the stress confinement times resulting in inefficient generation of pressure waves.

In view of the above, there remains a need for effective feedback mechanisms for monitoring phototherapy procedures.

SUMMARY

Embodiments of the method and system described herein make use of the temporal modulation of the light beam used to perform phototherapy or other procedures involving the interaction of a light beam with a biological medium, to provide practical feedback on the procedure and/or information on the medium.

In accordance with one aspect, there is provided a method for monitoring, in real-time, a procedure on a biological medium using a light beam, the method comprising:

a) providing a photoacoustic frequency response characterizing said procedure;
b) selecting a feedback modulation frequency for the light beam based on the photoacoustic frequency response;
c) generating said light beam according to optical parameters selected to perform said procedure through interaction of the light beam with the biological medium, the optical parameters comprising an intensity modulation at the feedback modulation frequency; and
d) monitoring a photoacoustic feedback signal from the biological medium in real-time during said procedure.

In some implementations, the monitoring of step d may include filtering said photoacoustic feedback signal around the feedback modulation frequency. This filtering of the photoacoustic feedback signal is for example performed over a filtering bandwidth selected within a range between 0.01 and 10 MHz.

In some implementations, the feedback modulation frequency is selected within a range extending between 0.1 and 100 MHz.

In some implementations, the optical parameters of the light beam include a wavelength selected within a range extending between 450 and 1070 nm. The optical parameters of the light beam may also include an initial temporal profile defining one or more initial light pulses each having an initial pulse duration. The initial light pulses may be square-shaped or triangular-shaped. The initial light pulses may further define a train of initial sub-pulses. In one example, the feedback modulation frequency corresponds to a modulation period smaller than the initial pulse duration. The intensity modulation may have a varying amplitude over said initial pulse duration, and may vary over said initial pulse duration.

In some implementations, the intensity modulation may be a square wave, a triangular wave or a sinusoidal wave.

In some implementations, the method may include a preliminary step of measuring said photoacoustic frequency response.

In some implementations, the photoacoustic frequency response is based on at least one of laser parameters, sample properties and geometry, acoustic transmission properties of said biological medium and detector and amplification responses, and may be further based on a frequency dependant system noise of a system used to perform said procedure. The selecting of step b, may involve comparing the photoacoustic frequency response to this system noise, and selecting the feedback modulation frequency in association with an optimal SNR value identified through said comparing.

In some implementations, the selecting of step b, may involve comparing said photoacoustic frequency response to a frequency dependant system noise of a system used to perform said procedure, and optionally associating the feedback modulation frequency with an optimal SNR value identified through said comparing.

In some implementations, the monitoring of step d, may involve comparing variations in intensity, over time, of the photoacoustic feedback signal around said feedback modulation frequency and around a frequency associated with a micro-cavitation-induced acoustic contribution to detect a relative change indicative of the onset of micro-cavitation within said biological medium. This comparing may involve:
  filtering a first component of the photoacoustic feedback signal around the feedback modulation frequency;
  filtering a second component of the photoacoustic feedback signal around the frequency associated with a micro-cavitation-induced acoustic contribution to the photoacoustic frequency response; and
  calculating a ratio of the filtered first and second components over time.

In some implementations, the method may include an additional step e) of controlling said procedure based on the monitoring of the photoacoustic feedback signal, for example by modifying the optical parameters of the light beam.

In accordance with another aspect, there is provided a method for acquiring information from a biological medium interacting with a light beam, the method comprising:
a) imposing an intensity modulation on said light beam, said intensity modulation comprising a plurality of modulation frequencies;
b) monitoring a photoacoustic feedback signal resulting from the interaction of the light beam with said biological medium, said monitoring comprising:
  i) obtaining a photoacoustic feedback signal component related to each of said modulation frequencies; and
  ii) comparing said photoacoustic feedback signal components.

In some implementations, the obtaining of said photoacoustic feedback signal components involves filtering the photoacoustic feedback signal around each corresponding modulation frequencies. The comparing of the acoustic feedback components may include performing a ratiometric measurement of relative contributions of at least one pair of said photoacoustic feedback signal components.

In some implementations, the modulation frequencies may each correspond to a photoacoustic feedback frequency of a different constituent of the biological medium.

In some implementations, the plurality of modulation frequencies consists of a first and a second modulation frequency.

In accordance with another aspect, there is also provided a system for performing and monitoring, in real-time, a procedure on a biological medium, the system comprising:
  a light source generating a light beam according to optical parameters selected to perform said procedure through interaction of the light beam with said biological medium;
  a modulation controlling device coupled to said light source and configured to impose an intensity modulation on the light beam at a feedback modulation frequency;
  a modulation frequency selector operable to select said feedback modulation frequency based on a photoacoustic frequency response characterizing said biological medium upon interacting with modulated light; and
  an acoustic transducer coupled to the biological medium and configured to monitor an photoacoustic feedback signal from the biological medium in real-time during said procedure.

In some implementations, the modulation controlling device includes a driver connected to the laser source and modulating an operating current of the laser source or an external light modulator positioned in a path of the light beam downstream the laser source.

In some implementations, the modulation frequency selector includes a processor comprising a memory storing said photoacoustic frequency response.

In some implementations, the system may further include a processing unit configured to perform an analysis of the photoacoustic feedback signal and providing a feedback control signal to the light source.

In one embodiment, there is provided a method for monitoring in real-time a procedure on tissues in a biological medium, said procedure comprising of light-tissue interaction modulation in said tissues accompanied by a variation in a photoacoustic feedback signal from said biological medium, the method comprising:

a) selecting, based on predetermined acoustic response properties associated with said procedure, a modulation frequency providing a signal-to-noise ratio sufficient to allow a detection of said variation in the photoacoustic feedback signal;

b) generating a light beam having optical parameters selected to perform said procedure through interaction of the light beam with said tissues, said optical parameters including an intensity modulation at said modulation frequency; and c) monitoring the photoacoustic feedback signal resulting from the interaction of the light beam with said tissues.

The method may further include a step of filtering the monitored acoustic response signal around the modulation frequency or another frequency band.

The monitored acoustic signal may provide real-time feedback to the operator of the procedure, who can then take appropriate action. In other variants, the monitoring may trigger automatic adjustments or interruptions of the procedure.

The photoacoustic feedback response properties may for example be associated with the laser beam parameters, responses of the tissue sample (defined by its nature and geometry) and/or with a known response of sensors and/or amplifiers used in the phototherapy procedure. The method may involve a preliminary step of measuring these acoustic response properties.

In accordance with another embodiment, there is also provided a method for detecting an onset of micro-cavitation during a phototherapy procedure on tissues in a biological medium, said phototherapy procedure generating a photoacoustic feedback signal from said biological medium having a spectral content including a micro-cavitation-induced contribution, the method comprising:

a) generating a light beam having optical parameters selected to generate said micro-cavitation in the biological medium through interaction of the light beam with said tissues, said optical parameters including an intensity modulation at a modulation frequency;

b) monitoring the photoacoustic feedback signal resulting from the interaction of the light beam with said tissues, said monitoring comprising:

i) filtering the photoacoustic feedback signal around said modulation frequency;

ii) filtering the photoacoustic feedback signal around a frequency associated with the micro-cavitation-induced acoustic contribution; and iii) comparing the filtered signals of i. and ii. to detect a relative change indicative of the onset of micro-cavitation.

In accordance with yet another embodiment, there is provided a method for acquiring information from a biological medium interacting with a light beam, the method comprising:

a) imposing an intensity modulation on said light beam, said intensity modulation comprising a first modulation frequency and at least a second modulation frequency;

b) monitoring an photoacoustic feedback signal resulting from the interaction of the light beam with said biological medium, said monitoring comprising:

i) obtaining a first photoacoustic feedback signal component related to said first modulation frequency;

ii) obtaining a second photoacoustic feedback signal component related to said second modulation frequency (possibly more); and iii) comparing the first and second (and possibly more) photoacoustic feedback signal components.

The comparing above may involve a ratiometric measurement of the relative contributions of the first and second signal components to the photoacoustic feedback signal.

In some implementations, this method may be combined with some of the elements of the other methods described above to provide for the real-time monitoring of a phototherapy procedure or the like.

In some variants, the method may allow a comparative monitoring of different biological constituents in the biological medium, which may undergo alterations from the light beam at different moments in time.

In accordance with some embodiments, there is also provided a monitoring system for monitoring in real-time a light-induced procedure in a biological medium. The system includes:

a light source module configured for generating a light beam according to optical parameters selected to perform said procedure through interaction of the light beam with said biological medium. The light source module is configured to modulate the light beam at a at least one modulation frequency; and an acoustic monitoring module configured for monitoring the photoacoustic feedback signal resulting from the interaction of the light beam with said tissues.

a processing unit analysing spectral component(s) of the photoacoustic feedback signal.

In some embodiments, the modulation frequency may be selected, based on predetermined acoustic response properties associated with a phototherapy procedure or the like, to provide a signal-to-noise ratio sufficient to allow a detection of a variation in the photoacoustic feedback signal resulting from the interaction of the light beam with the biological medium.

In some embodiments, the acoustic monitoring module is configured for filtering the photoacoustic feedback signal around at least one frequency band. The acoustic monitoring module may filter the photoacoustic feedback signal around one or more modulation frequency, or around a frequency associated with a micro-cavitation-induced contribution. A processor may be provided to operate this filtering and optionally compare two or more filtered signals to detect a relative change indicative of the onset of micro-cavitation or to provide ratiometric measurements.

Other features and advantages of the invention will be better understood upon reading of preferred embodiments thereof with reference to the appended drawings.

BRIEF DESCRIPTION OF THE DRAWINGS

FIGS. 7A, 7B and 7C illustrate the initial optical pulse shape of a light beam for use in a phototherapy procedure, FIGS. 8A, 8B and 8C illustrate the applied intensity modulation, and FIGS. 9A, 9B and 9C illustrate the resulting treating light beam according to three examples.

DETAILED DESCRIPTION

Figure 1:
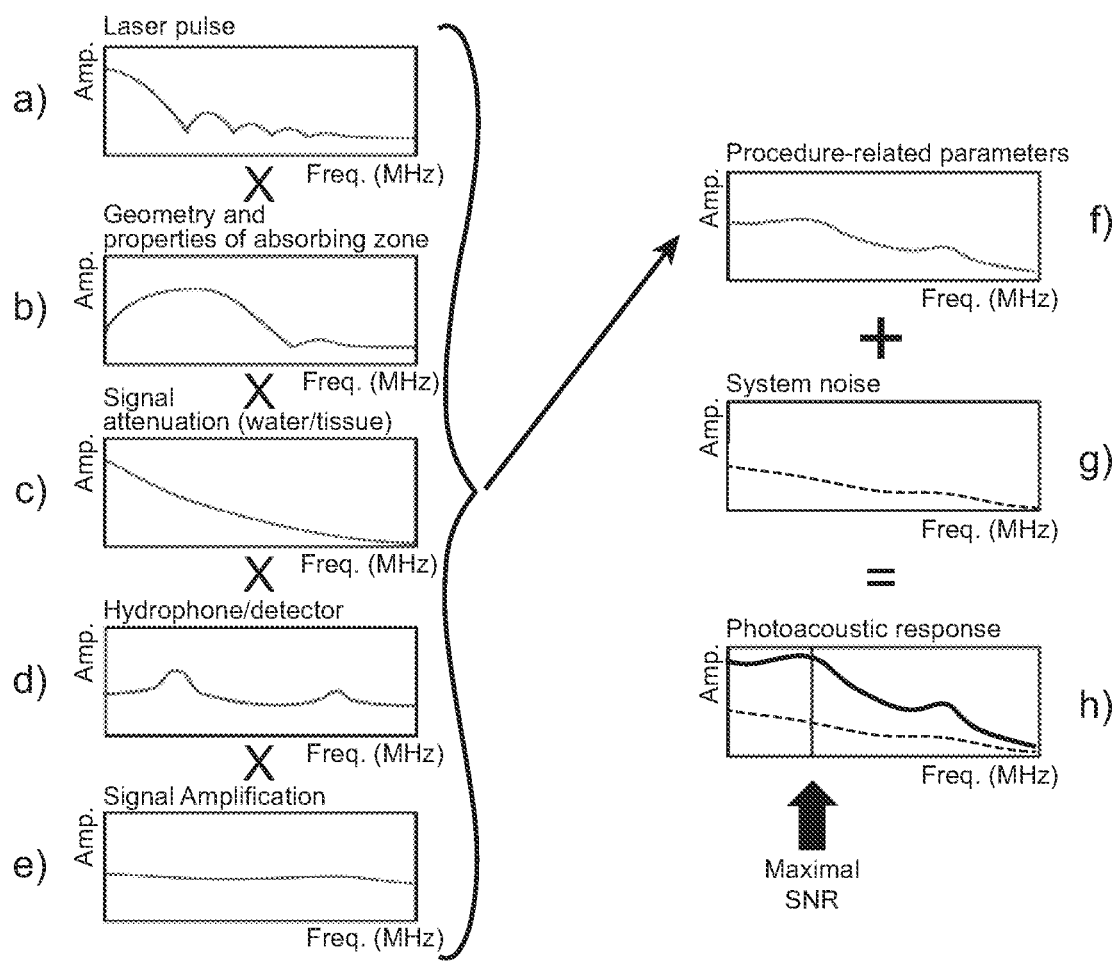
FIG. 1 schematically illustrates the factors influencing the photoacoustic frequency response.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Embodiments of the present method and system provide for the real-time monitoring of a light-induced procedure in a biological medium, and/or the acquisition of information related to this biological medium.

The present methods may for example be applied to phototherapy procedures on tissues of the eye or other biological medium. The expression "phototherapy" is understood to refer to the treatment or other alterations of tissues through light irradiation. It will however be readily understood that the present method may be applied to procedures other than phototherapy, such as tissue identification and imaging.

Embodiments of the present methods and systems may for example be of use in the context of a phototherapy procedure involving micro-cavitation. The phenomenon of "cavitation" may be understood as the formation of vapor cavities in a liquid. Small liquid-free zones or "bubbles" are formed as a result of forces acting upon the liquid. Micro-cavitation can occur in circumstances where the liquid is subjected to rapid changes of pressure, which leads to the formation of cavities in the liquid in areas where the pressure is relatively low. When subjected to higher pressure, the voids implode and can generate an intense shock wave. Laser-directed micro-cavitation involves the generation of vapor bubbles within a medium possessing a liquid phase, upon absorption of laser energy by the medium. The medium may be affected by both thermally-induced alterations resulting from heat diffusion within the medium, and by mechanically-induced alterations originating from stresses developing in the medium as the micro-cavitation bubbles expand and collapse. In the description below, the reference to "alterations" of a medium through micro-cavitation may encompass either thermally-induced alterations, mechanically-induced alterations or both. Particularly, in the case of biological media (such as, for example, living organisms or tissue), the medium can be homogeneous or heterogeneous and the "alterations" may affect the structure or the biological function of the organism, or both.

The expression "micro-cavitation" is typically used to refer to processes leading to the generation of transient bubbles of micrometric dimensions, but it will be generally understood that the use of language such as "micro-cavitation" or "microbubble" is not meant to impart any specific size limitations to the physical phenomena to which the present invention may apply.

Local photo-induced temperature gradients and/or pressure gradients in treated tissues typically generate acoustic waves which travel through the tissue and which, as mentioned above, can be used for monitoring purposes as a photoacoustic feedback signal. The term "acoustic," as used herein, relates to longitudinal mechanical waves propagating through a medium. One skilled in the art will readily understand that the term "acoustic wave" and related uses of the adjective "acoustic" are meant to encompass waves having frequencies associated with both sounds and ultrasounds, and that frequencies in the acoustic domain include ultrasonic frequencies.

Procedures involving the photostimulation of a biological medium will generate a photoacoustic feedback signal, that is, an acoustic wave resulting from the interaction of the light beam used for the procedure with the medium. Mechanical processes such as micro-cavitation or thermal processes from light-matter interactions may be at the origin of this photoacoustic feedback signal. The photoacoustic feedback signal can be monitored with an adequate transducer. The amplitude and temporal shape of the photoacoustic feedback signal strongly depend on local energy absorption in the biological medium, and can therefore serve for dosimetry purposes. Alterations of the treated tissues are generally accompanied by a variation in the photoacoustic feedback signal, which can be used to monitor the progress on the phototherapy procedure. However, for light beams typically used in phototherapy, for example light pulses having a duration from a few microseconds to a few milliseconds, only modest photoacoustic signals are generated at the onset and offset of the light pulses.

In other embodiments, the methods described herein may also be used in the context of procedures on media outside of biological applications. For example, modulated laser pulses are used for precise micromachining or laser engraving of samples of different types, for example metals or polymers. The sample is placed in a tank filled with water or another medium in which acoustic waves can propagate. As the sample is heated with the modulated laser pulse, a photoacoustic wave is produced. An acoustic transducer records the photoacoustic feedback signal and provide an indirect measurement of the level of energy absorbed. Spectral analysis can be used to isolate the ultrasound generated at the laser modulation frequency. In another example, laser pulses of 50-250 ns are used for material welding. Pulse modulation and frequency domain photoacoustic sensing can be used to monitor in real time the energy absorbed at the welding interface. Again, a closed loop system can help control the laser energy in real-time allowing a precise welding.

Process for Photoacoustic Phototherapy Feedback with Modulated Light Excitation

In accordance with one aspect, the present method may involve imposing an intensity modulation on the light beam used for a phototherapy or other procedures involving the interaction of a light beam with a biological medium. The method also involves selecting a frequency for this intensity modulation, referred to herein as the "feedback modulation frequency". Preferably, the feedback modulation frequency is selected such that it will generate a photoacoustic feedback signal at the same frequency. The acoustic range in this context may encompass sonic and ultrasonic frequencies, for example between 0.1 and 100 MHz. In some implementations, the modulation frequency may be selected between 0.1 and 20 MHz. The selection of the modulation frequency is preferably based on a photoacoustic frequency response characterizing the procedure, as explained further below.

The method further involves generating a light beam having optical parameters selected to perform phototherapy or another procedure through interaction of the light beam with a target biological medium. The optical parameters of the light beam may include a wavelength in a range of 450-1070 nm. In some variants, the light beam may be embodied by a single pulse having a pulse duration of about 0.1 to 100 µs. Other optical parameters characterizing the light beam include the beam diameter at the treatment site, pulse shape, peak laser fluence, etc. The optical parameters of the light beam further include an intensity modulation at the selected feedback modulation frequency. Modulation can be achieved with square waves, sinusoidal, triangular or other periodic patterns with modulation frequency ranging from 0.1 to 100 MHz. In other variants, the light beam may define a train of sub-pulses each having a duration and repetition rate of >1 ps and >10 GHz respectively.

In some variants the light beam may define one or more pulses prior to the imposition of the intensity modulation, and the optical parameters of the light beam therefore include an initial temporal profile defining one or more initial light pulses each having an initial pulse duration. The initial temporal profile of the light beam may take a multitude of shapes depending on the implementation and application. FIGS. 7A-7C, 8A-8C and 9A-9C respectively illustrate examples of an initial shape of the light beam, the intensity modulation imposed on the initial light beam and the resulting modulated light beam used for performing the procedure. Example A shows a square-shaped pulse having an initial pulse duration (FIG. 7A), modulated by a square wave (FIG. 8A) having a constant frequency defining a period smaller than the initial pulse duration. The resulting modulated light beam is illustrated in FIG. 9A, and takes the shape of a series of sub-pulses at a repetition rate determined by the modulation signal, and of total duration corresponding to the initial pulse duration. In example B, the initial pulse is shown having a triangular shape with a positive slope (FIG. 7B), and the modulation signal defines a non-zero periodic oscillation (FIG. 8B), resulting in a signal shape defining a periodic oscillation of gradually increasing intensity (FIG. 9B). Finally, example C illustrates a more complex case where the initial light beam includes a train of sub-pulses, for example in the picosecond range (FIG. 7C), modulated by a modulation signal of varying frequency (FIG. 8C), resulting in a series of picosecond sub-pulses of variable intensity (FIG. 9C). Of course, examples A, B and C are given for illustrative purposes only.

The generated light beam can be used for performing a phototherapy procedure in a manner known in the art and using any phototherapy setups. The photoacoustic feedback signal resulting from the interaction of the light beam with the tissues is then monitored.

Throughout a typical phototherapy procedure, the spectral signature of the photoacoustic feedback signal, i.e., the profile of the power spectral density of this signal as a function of frequency, may be influenced by several factors, which collectively define the photoacoustic frequency response characterizing the procedure. The photoacoustic frequency response may be defined as the spectral variation of an acoustic wave which would travel through the biological medium upon stimulation by a laser beam having a pulse duration shorter than the stress relaxation time constant.

FIG. 1 illustrates various such factors which may contribute to the spectral composition of the photoacoustic frequency response. Since the pressure generated within the biological medium by the light beam is directly dependent on the laser fluence, the laser pulse shape and the energy deposition rates are factors which have an impact on the photoacoustic frequency response. In some implementations, the photoacoustic frequency response depends on the pulse shape and pulse duration (FIG. 1 graph a)). The photoacoustic frequency response also varies with the properties and geometry of the absorbing region within the biological medium, including the size of the absorbers, the concentration of the absorbers and the size of the laser spot (see FIG. 1 graph b)), and the absorption and physical properties of the material and the speed of sound within them (FIG. 1 graph c)). The characteristic response as a function of frequency of the detector (FIG. 1 graph d)) and the electronic amplifying circuit (FIG. 1 graph e)) used to measure the photoacoustic feedback signal also influence its spectral content. As a result, the photoacoustic frequency response characterizing the procedure typically includes a convolution of laser parameters, sample properties and geometry, surrounding tissue acoustic transmission properties, detector and amplification responses, as portrayed in FIG. 1 graph f). All of these parameters relate to aspects of the procedure and it's monitoring, leading to a spectral signature associated with a particular procedure.

The photoacoustic frequency response also depends on system noise associated with the system and devices used to perform the procedure (see FIG. 1 graph g)). The system noise may be viewed as the spectral variation of an acoustic signal which would be measured from the medium in the absence of optical stimulation. The noise is added to the spectral signature of procedure-related parameters explained above and may obscure some of the photoacoustic response, limiting the sensitivity of the system. As shown in FIG. 1 graph h) the photoacoustic frequency response may be viewed as a combination of the spectral signature of procedure-related parameters and the frequency dependent system noise.

It will be readily understood that in some implementations, only some of the above factors may be considered in determining the photoacoustic frequency response associated with the procedure. For example, in some implementations, one or a few of the factors influencing the photoacoustic frequency response may be dominant over the others, and their determination may suffice to properly characterize the photoacoustic frequency response. In some cases, for example, the dominant contributor to the photoacoustic frequency response may be governed by the treating pulse duration. In other cases, the dominant contribution to this response may be the spectral signature of a transducer or amplifier used in the monitoring system.

In some implementations, the selection of the modulation frequency involves comparing the photoacoustic frequency response to the system noise, as shown in FIG. 1 graph h). The feedback modulation frequency is then selected in association with an optimal SNR value identified through this comparison.

Figure 2A:
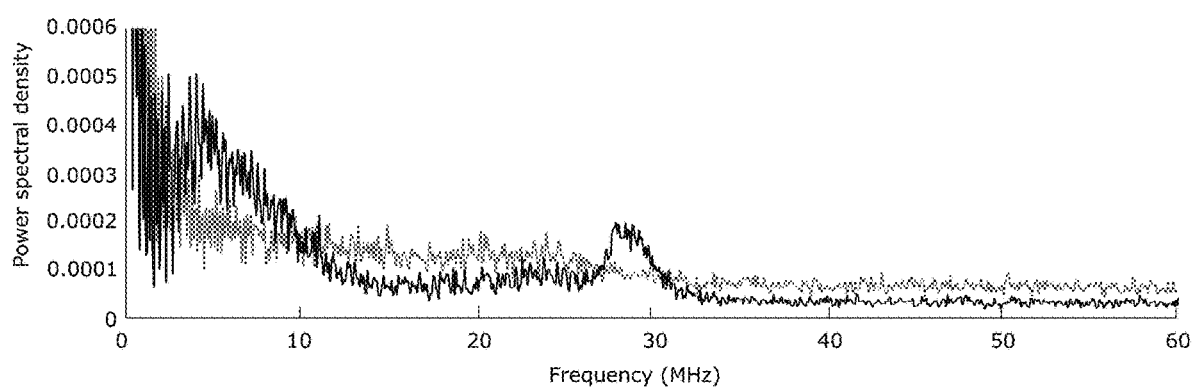
FIG. 2A is a graph of the averaged response signal of a phototherapy environment to a 3 ns pulse (black) compared to noise from this environment (grey)

FIG. 2A shows an example of the photoacoustic frequency response of a given phototherapy environment. The expression "phototherapy environment" is understood herein to be the combination of a specific phototherapy system and setup and a specific biological medium in which the procedure is to be performed, taking therefore into account all the factors listed above as influencing the photoacoustic frequency response. The black curve illustrates the frequency response of the environment when irradiated with a 3 ns light pulse, insufficient to generate significant alterations in the biological medium, whereas the grey curve illustrates the system noise. As can be seen, some frequency ranges provide a SNR allowing a clearer distinction of the signal over the noise. These ranges show as peaks in the photoacoustic frequency response around 5 MHz and 28 MHz in the illustrated example of FIG. 2A.

In some embodiments, the present method may include a preliminary step of measuring one or more photoacoustic waves from the biological medium in order to evaluate the photoacoustic frequency response of the procedure. This may for example be achieved by sending a test light pulse having parameters insufficient to alter the biological medium, such as was done to obtain the results of FIG. 2A. In other variants, the photoacoustic frequency response may be predetermined based on intrinsic properties of the biological medium and/or of the system used to perform the phototherapy and monitoring procedure. The photoacoustic frequency response may for example be evaluated based on previously performed measures, information from literature, calibration curves of the devices used for the procedure, etc. The method may also involve prompting the operator for procedure specific parameters such as the geometry and properties of the absorbing zone, the laser parameters, etc, and provide an optimal feedback modulation frequency based on the collected information and related pre-existing data.

In some implementations, the present method may include a step of filtering the photoacoustic feedback signal around the feedback modulation frequency. This filtering may be performed over a filtering bandwidth selected within a range of a few MHZ, for example between 0.01 and 10 MHz. As will be readily understood by one skilled in the art, the expression "filtering" is understood to refer to any manner of isolating, extracting or otherwise emphasizing the portion of the photoacoustic feedback signal around the frequency of interest. For example, the filtering may include the use of lock-in amplification, analog electronic bandpass filters, spectral analyzers, digitization and digital spectral analysis.

Figure 2B:
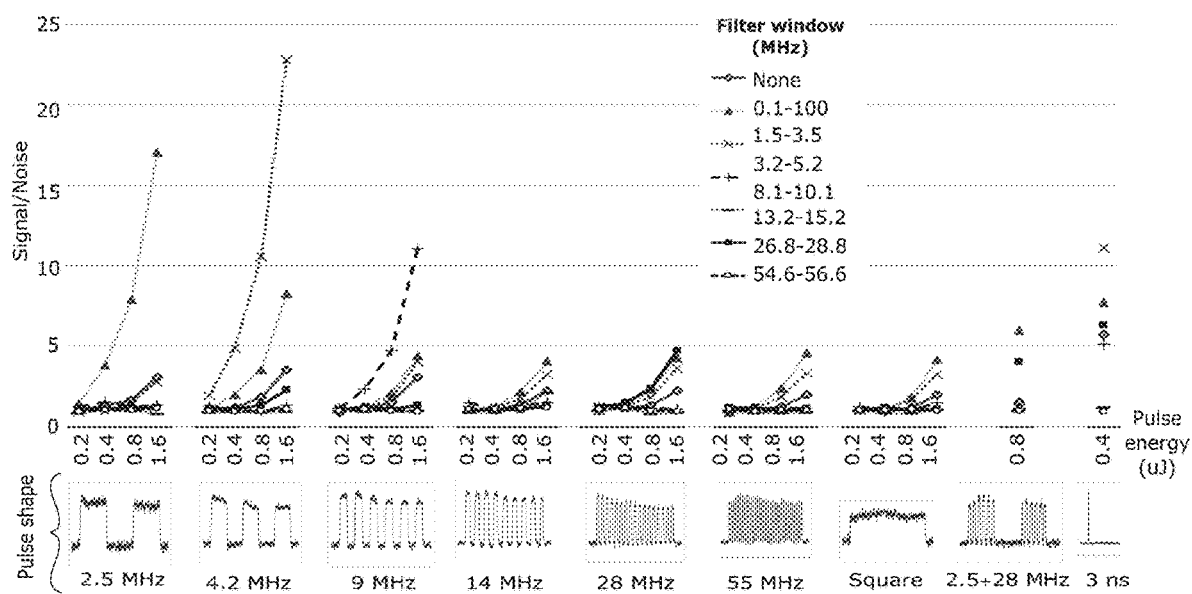
FIG. 2B shows the filtered signal-to-noise ratio obtained using different feedback modulation frequencies and filtering ranges.

FIG. 2B shows the signal-to-noise ratios obtained with different feedback modulation frequencies and detection filtering properties for an exemplary phototherapy procedure, performed in the environment of FIG. 2A. Representative pulse shapes of the modulated light beam used for each experiment are illustrated below the x-axis. Each pulse shape is a combination of a single light pulse of duration of 600 ns on which has been imposed a square wave intensity modulation at the feedback modulation frequency indicated below the graph. Each data point is the average of 8 photoacoustic measurements. In this example, the maximal signal-to-noise ratio is achieved with a modulation frequency of approximately 5 MHz (4.2 MHz) and filtering around this frequency.

The results of FIG. 2B indicate that in this example, the best SNR values were obtained through the modulation of the light beam at the optimal modulation frequency and the filtering of the photoacoustic feedback signal around this same frequency. This has been found to be a reliable approach, especially for phototherapy applications in the thermoelastic regime. Advantageously, the filtering may be performed over a relatively small bandwidth, of the order of a few MHz. However, in some other implementations the modulation of the treating light beam may be sufficient to provide a useful gain in SNR sufficient to allow detection and monitoring, without the related filtering of the photoacoustic feedback signal.

The example of FIG. 2B illustrates the use of square waves at various modulation frequencies imposed on a single light pulse, resulting in the light beam taking the shape of a train of light sub-pulses. In other embodiment, the intensity modulation may be a non-zero function which could for example provide as a result a single light pulse having a different shape, as illustrated in the example of FIG. 9B.

In some embodiments, the present method may be characterized as follows:
1) A modulated light beam for treatment and generation of a photoacoustic feedback signal within a volume of tissue or absorbing material where modulation shapes are determined by matching the acoustic response properties or resonances of the sample (defined by its nature and geometry) sensors and/or amplifiers;
2) Measurement of the generated acoustic waves with an acoustic sensor which convert the photoacoustic feedback signal into an electrical signal;
3) Optionally filtering of sensor signal to remove noise outside of the modulation frequency(ies) employed and expected to be measured, to generate a feedback for a phototherapeutic treatment.

Process for Micro-Cavitation Detection with Modulated Light Excitation in Biological or Other Samples In other words, the modulation and acoustic signal filtering properties are preferably chosen to accommodate the photoacoustic frequency response of the system for an enhanced treatment feedback.

In some implementations, the method above may be of use to detect the onset of micro-cavitation during a phototherapy procedure on tissues in a biological medium.

Modulated photoacoustic feedback signals can serve for micro-cavitation detection, which is related to treatment efficacy for some phototherapies. When the micro-cavitation threshold is reached, the light-tissue interaction is no longer in the thermoelastic regime and both the waveform and amplitude vs light fluence relationships of the photoacoustic feedback signal are changed. Moreover, the spectral signature of the acoustic wave is affected by the light-tissue interaction regime. In the thermoelastic regime, the spectral content of the photoacoustic feedback signal is dependent on the spectral content of the treating light beam. Beyond the thermoelastic threshold, when micro-cavitation occurs, additional acoustic frequencies are generated. The spectral content of the photoacoustic feedback signal therefore includes a "micro-cavitation-induced contribution".

In some implementations, the monitoring of the photoacoustic feedback signal as presented above may involve comparing variations in intensity, over time, of the photoacoustic feedback signal around both the feedback modulation frequency and around a frequency associated with the micro-cavitation-induced acoustic contribution. A relative change indicative of the onset of micro-cavitation within the biological medium can be detected in this manner.

By way of example, this aspect may be performed by filtering a first component of the photoacoustic feedback signal around the feedback modulation frequency, filtering a second component of the photoacoustic feedback signal around the frequency associated with a micro-cavitation-induced acoustic contribution, and calculating a ratio of the filtered first and second portions over time. As mentioned above, the reference to "filtering" is meant to encompass numerous manners of isolating or enhancing the components of the photoacoustic feedback signal within the range or interest.

In some embodiments, the method according to the present embodiment may therefore involve generating a light beam having optical parameters selected to generate micro-cavitation in the biological medium through interaction of the light beam with the tissues, the optical parameters including an intensity modulation at a modulation frequency. The method further includes monitoring the photoacoustic feedback signal resulting from the interaction of the light beam with the tissues. A loss of acoustic signal in the modulated frequency range can be indicative of micro-cavitation events or other non-linear events. The monitoring of the photoacoustic feedback signal may include filtering copies of this signal around the modulation frequency and around a frequency associated with the micro-cavitation-induced contribution. A comparison of these filtered signals allows detection of a relative change indicative of the onset of micro-cavitation.

Figure 3A:
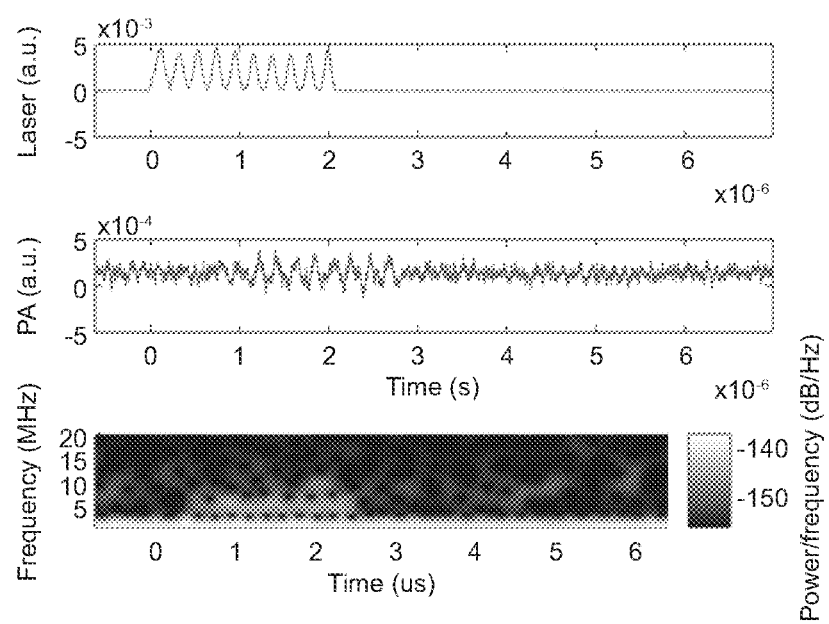
FIGS. 3A and 3B show the modulated light beam (upper panel), the photoacoustic feedback signal (middle panel) and a spectrogram of the photoacoustic feedback signal (lower panel), respectively in thermoelastic regime (FIG. 3A) and above micro-cavitation threshold (FIG. 3B) of a phototherapy procedure.
Figure 3B:
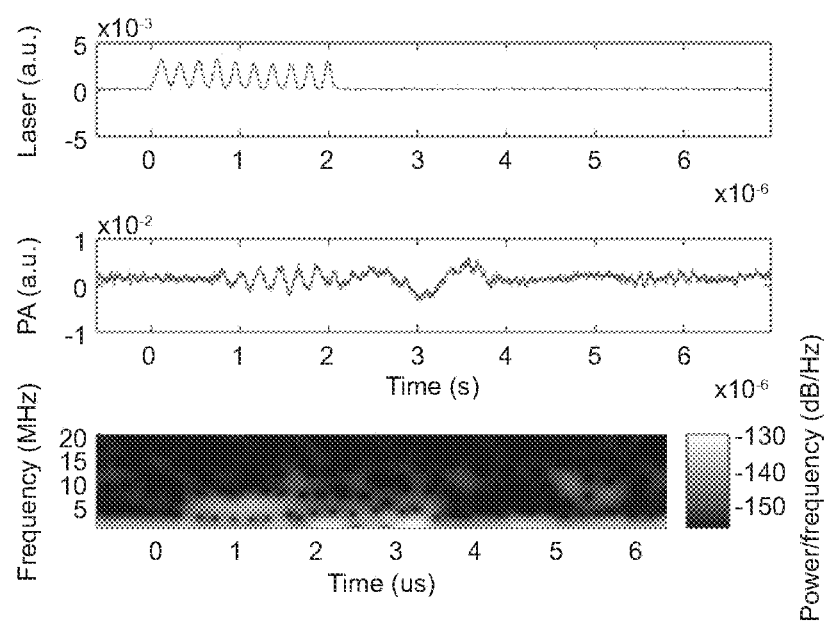
Figure 4:
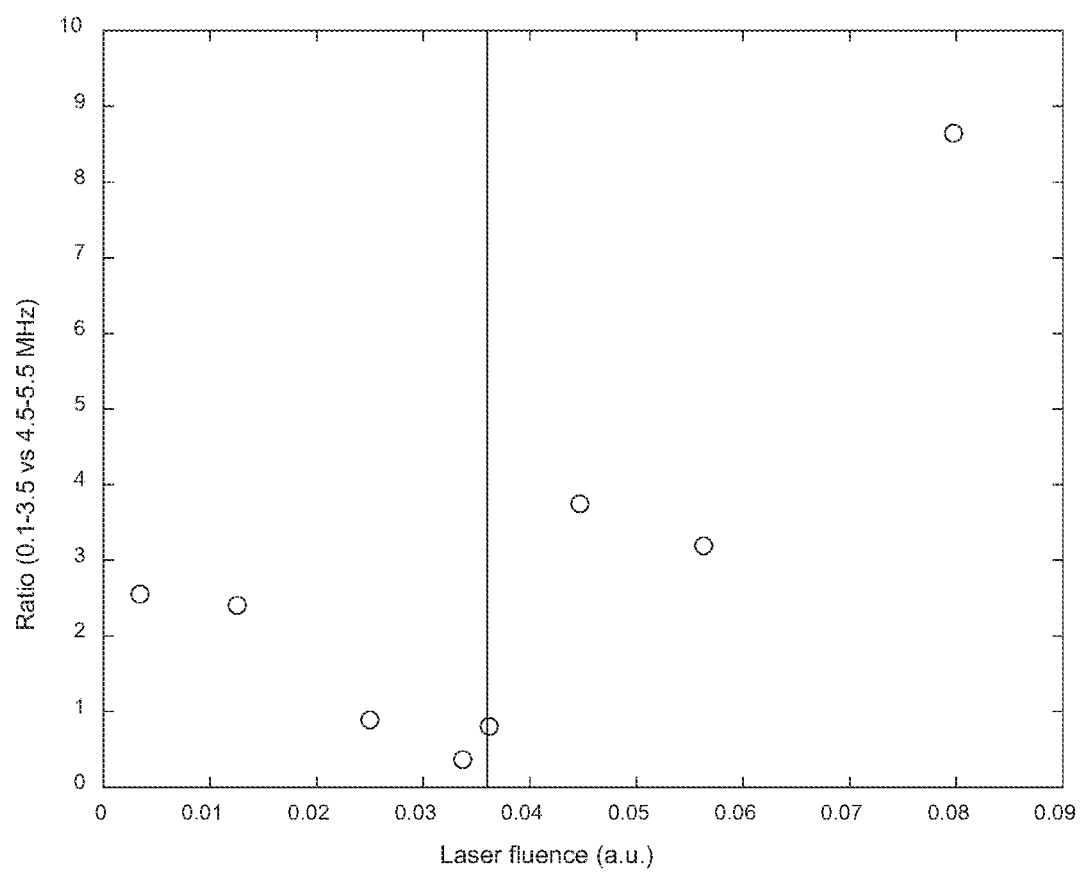
FIG. 4 is a graph illustrating the evolution, as a function of laser fluence, of the ratio of power spectral density filtered at 0.1-3.5 and 4.5-5.5 MHz respectively for the phototherapy procedure of FIGS. 3A and 3B.

FIGS. 3A, 3B and 4 illustrate the impacts of the above described modulation and filtering approach. FIG. 3A shows the pulse shape of the modulated light beam (upper panel), the generated acoustic wave (middle panel) and the acoustic wave spectrogram (lower panel) in thermoelastic regime. The same information for stimulation above micro-cavitation threshold is shown in FIG. 3B. The biological medium in this example was rabbit retinal explants, and the modulation frequency was around 5 MHz. It can be observed on the right-side spectrogram (FIG. 3B) that at the onset of cavitation, at about 3 µs, the signal contribution around 5 MHz disappears and higher contributions at lower frequencies appear. The ratio between filtered signals detected in spectral windows respectively surrounding the cavitation-related contributions (0.1-3.5 MHz) and the modulation frequency (4.5-5.5 MHz) changes with micro-cavitation occurrences, as illustrated in FIG. 4. This ratio, or an equivalent comparison factor, can therefore be monitored to provide real-time information on the onset of micro-cavitation.

In some embodiments, the present method may be characterized as follows:
1) a modulated excitation light for treatment and generation of a photoacoustic feedback signal within a volume of tissue or absorbing material where modulation are chosen to have a narrow spectral signature (bandwidth <1 MHz);
2) measurement of the generated photoacoustic feedback signal with an acoustic sensor;
3) filtering of photoacoustic feedback signal around feedback modulation frequency employed
4) filtering of photoacoustic feedback signal around acoustic frequency(ies) generated by the micro-cavitation(s) formation.
5) Comparison of acoustic frequencies inside and outside the feedback modulation frequency bands (for example around micro-cavitation-induced frequencies) or the evolution of a given frequency band within and after the treating pulse occurrence to assess for cavitations (micro-cavitations) detection.

This method for cavitation detection offers the advantage of being independent of the amplitude of the photoacoustic feedback signal, which could be influenced by other experimental factors.

Process for Ratiometric Measurement with Modulated Light Excitation

In accordance another aspect, there is provided a method for acquiring information from a biological medium interacting with a light beam. The method involves imposing an intensity modulation on the beam, with the intensity modulation including two distinct modulation frequencies (or more), for example a first modulation frequency and a second modulation frequency. A ratiometric comparison of the resulting acoustic signals at each frequency can be performed with a process similar to the one employed for cavitation detection.

In one embodiment, the method includes monitoring the photoacoustic feedback signal resulting from the interaction of the light beam with the biological medium under study. This monitoring involves obtaining a photoacoustic feedback signal component related to each of modulation frequency and comparing these photoacoustic feedback signal components. This may for example be accomplished by filtering the photoacoustic feedback signal at or around the corresponding modulation frequency, such as by isolating or amplifying the portion of the photoacoustic feedback signal which is related to the corresponding modulation of the optical signal.

Figure 10:
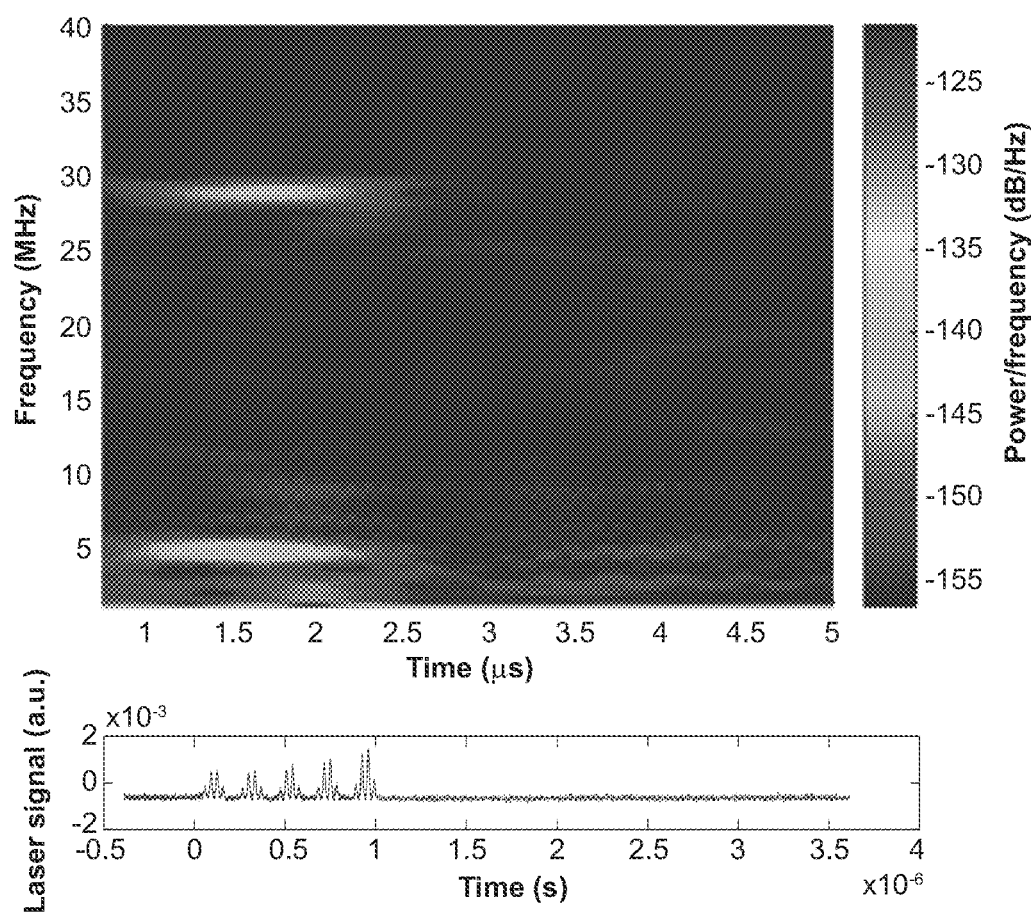
FIG. 10 illustrates a ratiometric approach using two different modulation frequencies.

The comparing above may involve a ratiometric measurement of the relative contributions of the first and second signal components to the acoustic feedback signal. This allows ratiometric photoacoustic information to be obtained, providing not only laser dosage feedback but also information about the nature of the laser absorbing targets, or different constituents of the biological medium. By way of example, if different constituents have characteristic photoacoustic responses at different frequencies, a first particle of the biological medium may provide a photoacoustic feedback at the first modulation frequency whereas a second particle provides photoacoustic feedback at the second frequency, the ratiometric approach of the present embodiment therefore enabling a measure of the relative proportions of both particles in the biological medium. An example of the data that can be obtained to perform this analysis is shown in FIG. 10.

In some implementations, the modulation approach described herein may be used as an investigating tool to characterize a medium without being related to the monitoring of a procedure. Of course, it will be understood that the method is not limited to two modulation frequencies, and that any number of frequency bands may be used to modulate the optical signal. Several modulation frequencies and/or chirped signals can help perform supplemental photoacoustic spectroscopic measurement simultaneously or independently of photo-treatment. This could be used, for example, in ophthalmology for monitoring tissue nature, retinal diseases, foreign particles in the aqueous humor, or pharmacological agents.

In some embodiments, the present method may be characterized as follows:
1) a modulated light beam with more than one modulation frequency for treatment and generation of a photoacoustic feedback signal within a volume of tissue or absorbing material;
2) measurement of said generated photoacoustic feedback signal with an acoustic sensor;

3) filtering of photoacoustic feedback signal around modulation frequencies employed;
4) Comparison of photoacoustic feedback signal components around selected modulation frequencies.

System

Figure 5:
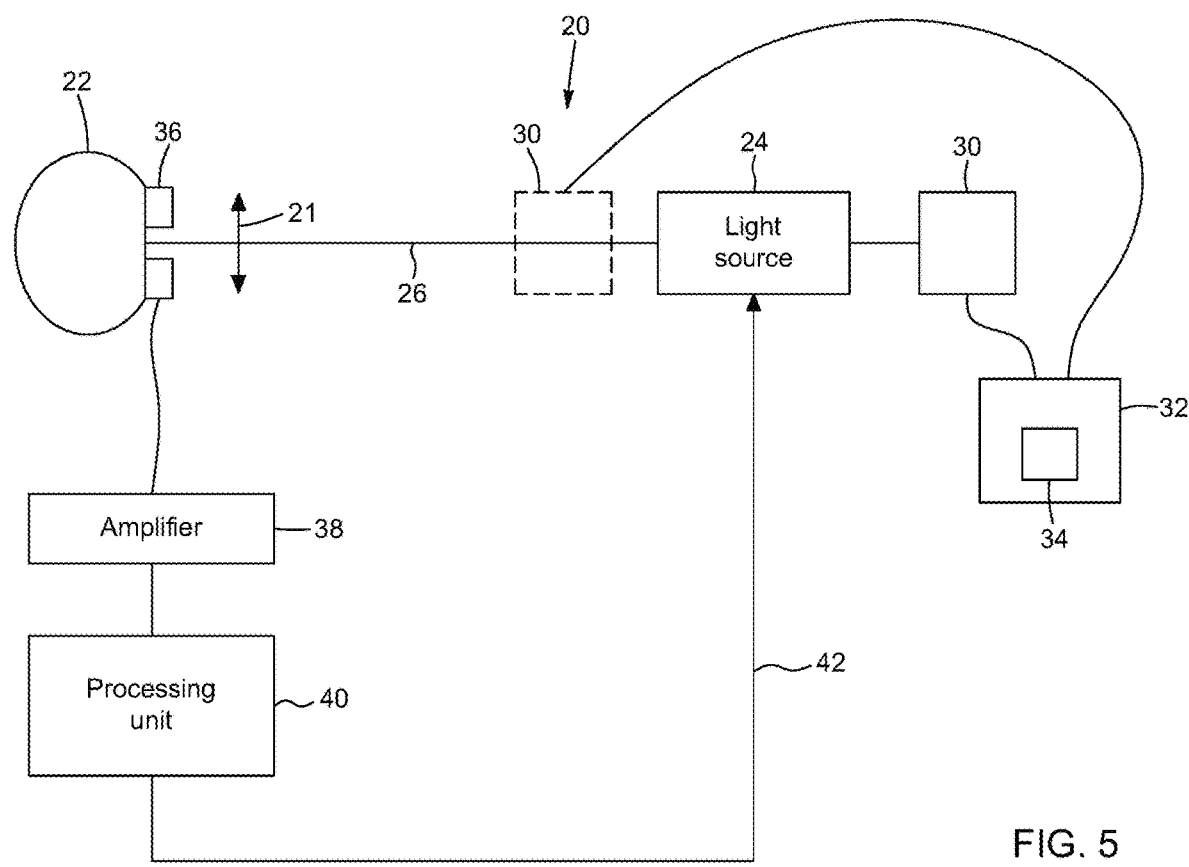
FIG. 5 schematically illustrates a system according to one embodiment.

Referring to FIG. 5, there is shown an example of a system 20 for performing and monitoring, in real-time, a procedure on a biological medium 22. In a possible embodiment, the system 20 may for example be an ophthalmic surgery system which employs a treating light beam for tissues which is directed through a lens 21 and is focused onto the retina embodying the biological medium 22.

The system 20 includes a laser source 24 generating a light beam 26 according to optical parameters selected to perform the desired procedure through interaction of the light beam 26 with the biological medium 22. The laser source 24 may for example be embodied by a solid state q-switched laser or a programmable fiber laser.

The system 20 further includes a modulation controlling device 30 coupled to the light source 24 and configured to impose an intensity modulation on the light beam 26 at a feedback modulation frequency. The modulation controlling device 30 may for example include a driver connected to the laser source 24 and modulating the operating current of the laser source 24, therefore modulating the light beam as it is generated. In other variants, the modulation controlling device may include an external light modulator positioned in a path of the light beam 26 downstream the laser source 24, therefore imposing the intensity modulation on the light beam subsequently to its generation.

The system 20 further includes a modulation frequency selector 32 operable to select the feedback modulation frequency based on a photoacoustic frequency response characterizing the biological medium 22 upon interacting with modulated light, for example as explained above. The modulation frequency selector may be embodied or include a processor having a memory 34 storing one or more photoacoustic frequency response(s), and may further include a non-transitory computer readable storage medium with a computer program stored thereon, the computer program being operable to select the feedback modulation frequency based on the photoacoustic frequency response of an acoustic transducer coupled to the biological medium and configured to monitor a photoacoustic feedback signal from the biological medium in real-time during said procedure.

The system further includes an acoustic transducer 36 coupled to the biological medium 22 and configured to monitor the photoacoustic feedback signal from the biological medium 22 in real-time during the procedure. The acoustic transducer may for example be embodied by a piezoelectric or an optical acoustic transducer.

The system may further include an amplifier 38 amplifying the acoustic signal from the transducer, and a processing unit 40 extracting and processing the information from the acoustic feedback signal. The processing unit can be configured to perform an analysis of the photoacoustic feedback signal and provide a feedback control signal to the light source. In some implementations, a feedback loop 42 connecting the processing unit 40 and the laser source 24 may allow a control of the intensity of the light beam 26 in view of the observed properties of the photoacoustic feedback signal. The processing unit may be embodied by a non-transitory computer readable storage medium with a computer program stored thereon and operable to perform said analysis. In some implementations, the processing unit may be an analog device performing the required functions.

Example of an Implementation

Figure 6:
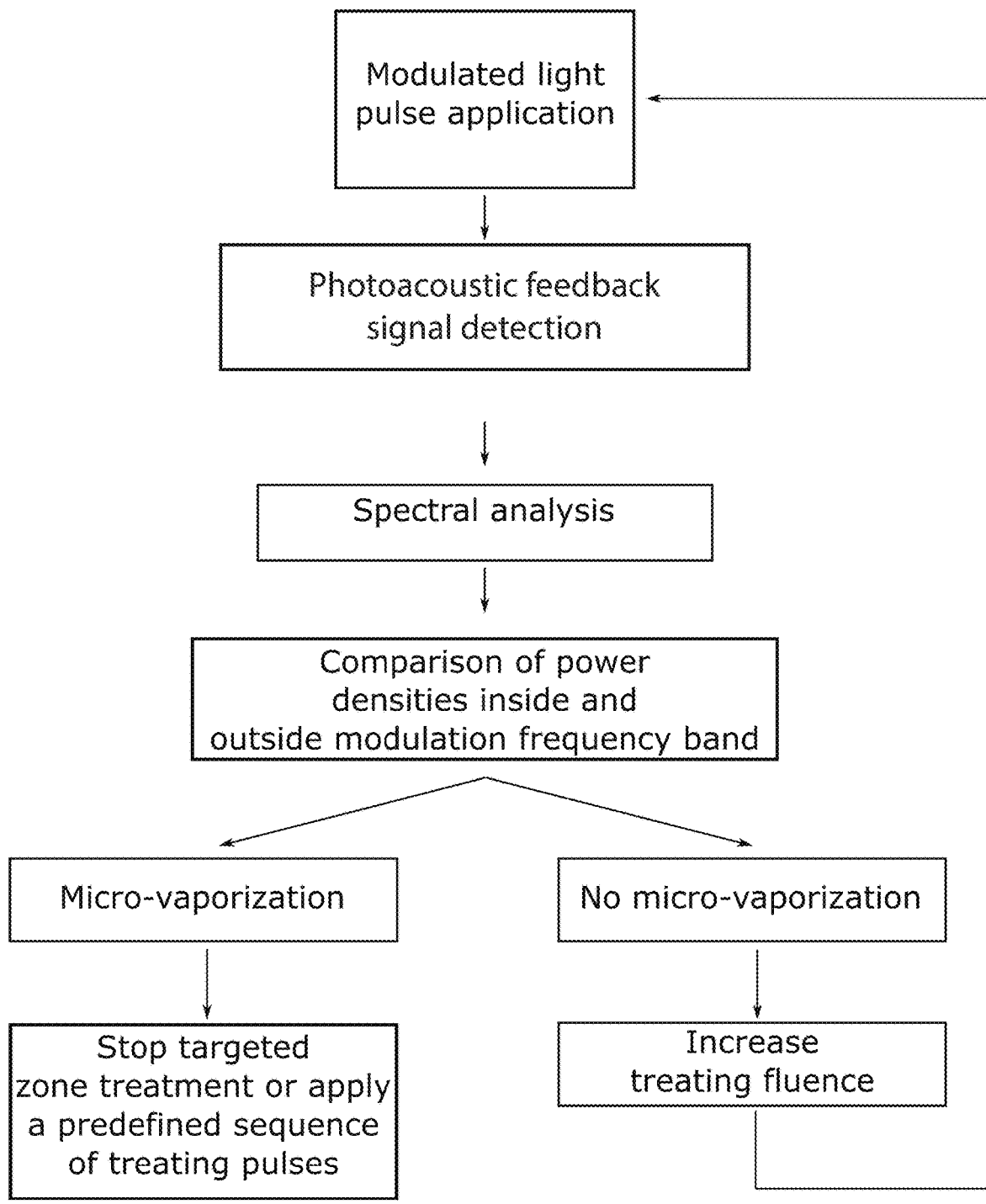
FIG. 6 is a flowchart of a process according to one embodiment applied to photoacoustic dosimetry in phototherapy.

Still referring to FIG. 5, and with additional reference to FIG. 6, there is shown a practical example of a phototherapy procedure embodying the methods described herein.

In this example, the light beam 26 is a modulated light pulse (single pulse with a modulation envelope, comprising a pulse train) with a narrow spectral content (bandwidth <1 MHz), and is delivered to the retina of a patient. Light is absorbed, and thermal expansion occurs in the retina which generates an acoustic wave. The photoacoustic feedback signal is detected. The spectral content of the photoacoustic feedback signal is analyzed using a spectrum analyzer, lock-in amplifier(s), boxcar averager(s) or software tools such as fast Fourier transforms algorithms. Alternatively, the photoacoustic feedback signal is replicated. One replicate is filtered around the modulation frequency band to extract the photo-induced thermoelastic acoustic variation from noise and the second replicate is filtered around one or more off-modulation frequency band to extract non-thermoelastic events such as cavitations. The ratio of the power density in each frequency band is indicative of a micro-cavitation occurrence (indeed in the presence of a cavitation there is a sharp decrease in the modulation frequency band power density and an increase of micro-cavitation induced frequencies). If a cavitation is detected, a possible action could be to maintain the same, or a different light fluence for a predetermined number of successive treating pulses or to stop photo-treatment. If no micro-cavitation is detected, the light fluence may be increased by a pre-determined incremental value. This process is to be repeated until the desired micro-cavitation outcome is reached for a given targeted zone. After which the treating beam is moved (manually or automatically) to the next area to be treated. A flowchart diagram of such an embodiment is presented in FIG. 6.

Of course, numerous modifications could be made to the embodiment described above without departing from the scope of the invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for monitoring, in real-time, a procedure on a biological medium using a light beam, the method comprising:
   a) providing a photoacoustic frequency response characterizing the procedure;
   b) selecting a feedback modulation frequency for the light beam based on the photoacoustic frequency response;
   c) generating the light beam according to optical parameters selected to perform the procedure, the procedure being performed through interaction of the light beam with the biological medium, the optical parameters comprising an intensity modulation at the feedback modulation frequency; and
   d) monitoring a photoacoustic feedback signal from the biological medium in real-time during the procedure.

2. The method according to claim 1, wherein the monitoring of step d. comprises filtering the photoacoustic feedback signal around the feedback modulation frequency.

3. The method according to claim 2, wherein the filtering of the photoacoustic feedback signal is performed over a filtering bandwidth selected within a range between 0.01 and 10 MHz.

4. The method according to claim 1, wherein the feedback modulation frequency is selected within a range extending between 0.1 and 100 MHz.

5. The method according to claim 1, wherein the optical parameters of the light beam include a wavelength selected within a range extending between 450 and 1070 nm.

6. The method according to claim 1, wherein the optical parameters of the light beam include an initial temporal profile defining one or more initial light pulses each having an initial pulse duration.

7. The method according to claim 6, wherein each of the one or more initial light pulses are square-shaped or triangular-shaped.

8. The method according to claim 6, wherein each of the one or more initial light pulses define a train of initial sub-pulses.

9. The method according to claim 6, wherein the feedback modulation frequency corresponds to a modulation period smaller than the initial pulse duration of each of the one or more initial light pulses.

10. The method according to claim 6, wherein the intensity modulation has a varying amplitude over the initial pulse duration of each of the one or more initial light pulses.

11. The method according to claim 6, wherein the feedback modulation frequency varies over the initial pulse duration of each of the one or more initial light pulses.

12. The method according to claim 1, wherein the intensity modulation is a square wave, a triangular wave or a sinusoidal wave.

13. The method according to claim 1, comprising a preliminary step of measuring the photoacoustic frequency response.

14. The method according to claim 1, wherein the photoacoustic frequency response is based on at least one of laser parameters, sample properties and geometry, acoustic transmission properties of the biological medium and detector and amplification responses.

15. The method according to claim 14, wherein the photoacoustic frequency response is further based on a frequency dependent system noise of a system used to perform the procedure.

16. The method according to claim 15, wherein the selecting of step b. comprises comparing the photoacoustic frequency response to the system noise, and selecting the feedback modulation frequency in association with an optimal SNR value identified through the comparing.

17. The method according to claim 1, wherein the selecting of step b. comprises comparing the photoacoustic frequency response to a frequency dependent system noise of a system used to perform the procedure.

18. The monitoring according to claim 17, wherein the feedback modulation frequency selected at step b. is associated with an optimal SNR value identified through the comparing.

19. The method according to claim 1, wherein the monitoring of step d. comprises comparing variations in intensity, over time, of the photoacoustic feedback signal around the feedback modulation frequency and around a frequency associated with a micro-cavitation-induced acoustic contribution to detect a relative change indicative of the onset of micro-cavitation within the biological medium.

20. The method according to claim 19, wherein the comparing comprises:

filtering a first component of the photoacoustic feedback signal around the feedback modulation frequency;

filtering a second component of the photoacoustic feedback signal around the frequency associated with a micro-cavitation-induced acoustic contribution to the photoacoustic frequency response; and calculating a ratio of the filtered first and second components over time.

21. The method according to claim 1, comprising an additional step e) of controlling the procedure based on the monitoring of the photoacoustic feedback signal.

22. The method according to claim 21, wherein the controlling of step e) comprises modifying the optical parameters of the light beam.

23. The method according to claim 1, wherein the feedback modulation frequency comprises a plurality of feedback modulation frequencies, wherein monitoring a photoacoustic feedback signal resulting from the interaction of the light beam with the biological medium comprises:

i. obtaining a photoacoustic feedback signal component related to each of the plurality of feedback modulation frequencies; and ii. comparing the photoacoustic feedback signal components.

24. The method according to claim 23, wherein the obtaining of the photoacoustic feedback signal components comprises filtering the photoacoustic feedback signal around each corresponding feedback modulation frequencies.

25. The method according to claim 23, wherein the comparing of the photoacoustic feedback signal components comprises performing a ratiometric measurement of relative contributions of at least one pair of the photoacoustic feedback signal components.

26. The method according to claim 23, wherein the feedback modulation frequencies each correspond to a photoacoustic feedback frequency of a different constituent of the biological medium.

27. The method according to claim 23, wherein the plurality of feedback modulation frequencies consist of a first and a second feedback modulation frequency.

28. A system for performing the method of claim 1 and monitoring, in real-time, a procedure on a biological medium, the system comprising:

a laser source generating a light beam according to optical parameters selected to perform the procedure through interaction of the light beam with the biological medium;

a modulation controlling device coupled to the light source and configured to impose an intensity modulation on the light beam at a feedback modulation frequency;

a modulation frequency selector operable to select the feedback modulation frequency based on a photoacoustic frequency response characterizing the biological medium upon interacting with modulated light; and an acoustic transducer coupled to the biological medium and configured to monitor a photoacoustic feedback signal from the biological medium in real-time during the procedure.

29. The system according to claim 28, wherein the modulation controlling device comprises (i) a driver connected to the laser source; and (ii) modulating an operating current of the laser source or an external light modulator positioned in a path of the light beam downstream the laser source.

30. The system according to claim 28, wherein the modulation frequency selector comprises a processor comprising a memory storing the photoacoustic frequency response.

31. The system according to claim 28, further comprising a processing unit configured to perform an analysis of the photoacoustic feedback signal and provide a feedback control signal to the laser source.

* * * * *